United States Patent [19]

Pogany et al.

[11] Patent Number: 5,217,712
[45] Date of Patent: Jun. 8, 1993

[54] BIOERODIBLE THERMOSET ELASTOMERS

[75] Inventors: Stefano A. Pogany; Gaylen M. Zentner, both of Lawrence, Kans.

[73] Assignee: Merck & Co., Inc., Rahway, N.J.

[21] Appl. No.: 715,951

[22] Filed: Jun. 17, 1991

Related U.S. Application Data

[62] Division of Ser. No. 409,908, Sep. 28, 1989, Pat. No. 5,047,464.

[51] Int. Cl.$^5$ .............................. A61K 31/74
[52] U.S. Cl. ............................. 424/78.18; 424/78.01; 424/78.08
[58] Field of Search ............... 424/78.18, 78.01, 78.08

[56] References Cited

U.S. PATENT DOCUMENTS 4,304,767 12/1981 Heller et al. .
4,549,010 10/1985 Sparer et al. .
4,735,804 4/1988 Caldwell et al. .
4,758,436 7/1988 Caldwell et al. .

OTHER PUBLICATIONS

"In Vitro and In Vivo Release of Levongestrel from Poly(ortho esters)", Heller et al., Journal of Controlled Release, 1(1985) 233-238.

Primary Examiner—Bernard Lipman
Attorney, Agent, or Firm—Francis P. Bigley; Joseph F. DiPrima

[57] ABSTRACT

Bioerodible, thermoset, covalently crosslinked, elastomeric poly(ortho ester)s are disclosed. These materials are comprised of polymer chains that are interlocked in a covalent, three dimensional network which imparts dimensional stability. Use of these thermoset, covalently crosslinked materials as a drug delivery device is also disclosed.

3 Claims, 4 Drawing Sheets

General Reaction Scheme

Monomeric Polyol    Diketene Acetal    Polymeric Polyol

Thermosetting Elastomeric Poly(ortho ester)

Sample 1

Sample 2

BIOERODIBLE THERMOSET ELASTOMERS

This is a division of application Ser. No. 409,908, filed Sep. 28, 1989 now U.S. Pat. No. 5,047,464.

BACKGROUND OF THE INVENTION

The reaction of diketene acetals with alcohols to produce poly (ortho ester)s was disclosed in U.S. Pat. No. 4,304,767. Known bioerodible poly(ortho ester)s, such as those described in U.S. Pat. No. 4,549,010, are comprised of linear polymer chains joined to one another by non-covalent intermolecular forces such as Van der Waal's dispersive forces and hydrogen bonding. These poly(ortho-ester)s are thermoplastic, i.e., their individual polymer chains slip by one another ("flow") if subjected to stress. This results in an irreversible deformation of the elastomers and accounts for their lack of resiliency when subjected to prolonged stress. Such characteristics are particularly disadvantageous in applications such as a gastric retention platform wherein the polymers, after having been subjected to stress during prolonged storage, are expected to behave in a resilient fashion.

A gastric retention platform, as disclosed in U.S. Pat. Nos. 4,735,804 and 4,758,436, is a drug delivery device comprised of a resilient polymer combined with an active ingredient. The platform is maintained in a first compressed state from the time of manufacture until ingestion. Subsequent to ingestion, the platform expands to a second relaxed state, thereby releasing the active ingredient to an environment of use (such as the stomach). The prolonged stress and strain suffered during storage limits the resilience of linear, thermoplastic polymer platforms and impedes their ability to expand to the second relaxed state subsequent to ingestion.

SUMMARY OF THE INVENTION

Covalently cross-linked poly(ortho ester)s are disclosed which exhibit greatly improved resiliency subsequent to prolonged periods of stress and strain as compared to previously known poly(ortho ester)s. The materials of the instant invention are thermoset, i.e., polymer chain slip is minimized under stress because the polymers are interlocked in a covalent, three-dimensional network. These thermoset, covalently cross-linked poly(ortho ester)s are synthesized by reacting either monomeric or polymeric polyols with diketene acetals.

It is a significant feature of this invention that monomeric polyols with a functionality of at least three, and/or polymeric polyols having a hydroxy functionality of at least two, must be used to produce the resilient, thermoset, covalently cross-linked bioerodible poly(ortho ester)s. Such monomeric or polymeric polyols do not exhibit resilient or elastic characteristics before reaction with diketene acetals. Rather, we have discovered that resiliency or elasticity is a latent property of those polyols that only becomes expressed upon reaction with diketene acetals to form the polymer. These polymers are suitable as carriers or matrices for drugs and other beneficial agents. Upon contact with an aqueous environment of use, the polymer degrades to release the drug or beneficial agent. The polymer may also constitute a structural member of a device requiring elasticity, resilience, and erodibility features.

DETAILED DESCRIPTION OF A PREFERRED EMBODIMENT

Polymeric polyols which can be reacted with diketene acetals to form the thermoset, covalently linked poly(ortho ester)s of the present invention include: Poly(butadiene) hydroxy terminated (PBD); Poly(isobutylene) hydroxyterminated (PIBD); Poly(isoprene) hydroxy terminated (PIPD); Poly(dimethylsiloxane) hydroxy terminated (PDMSD); Poly(butadiene-co-styrene) hydroxy terminated; Poly(ethylene-co-propylene) hydroxy terminated; and Poly(chloroprene) hydroxy terminated.

These polymeric polyols must have hydroxy functionality (number of hydroxyl groups per molecule) of at least two to effect polymerization with functionality greater than two effecting cross-linking. The above list is illustrative and is not meant to be limiting.

Monomeric polyols which may be admixed with the polymeric polyols and then reacted with diketene acetals to form the polymers claimed herein can be represented generally by the formula:

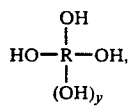

wherein R is a linear or branched hydrocarbon chain of 3 to 12 carbon atoms and y is 0 to 3. Typical monomeric polyols include: 1, 2, 6-hexanetriol; 2-ethyl-2-(hydroxymethyl)-1,3-propanediol; 1, 5, 10-decanetriol; and pentaerythritol; and the like.

Figure 1:
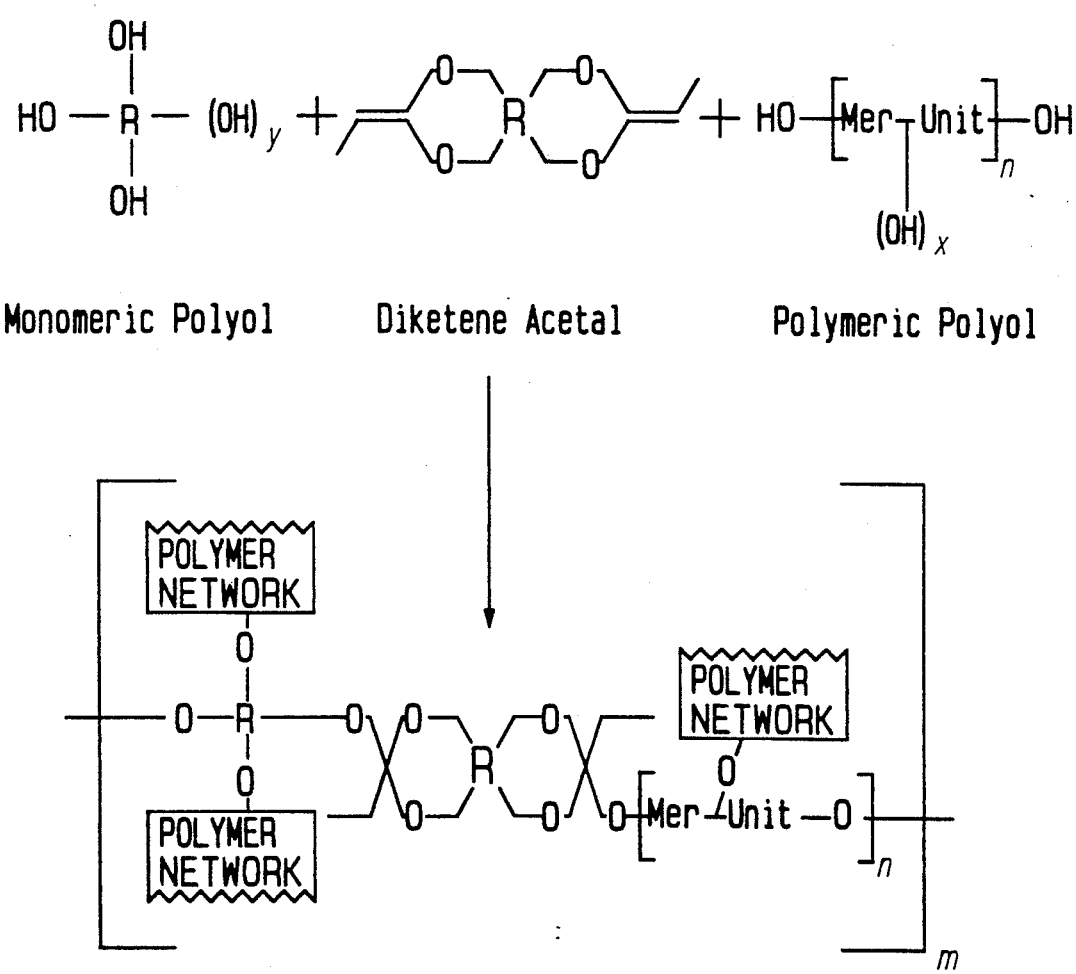
FIG. 1: illustrates the general reaction scheme used in making the thermoset, elastomeric poly (ortho ester)s of the instant invention.

A generalized reaction scheme for synthesizing the elastomers of the present invention is disclosed in FIG. 1.

A representative list of acceptable diketene acetals which will react with the aforementioned polyols to form our resilient, thermoset polymers is disclosed in U.S. Pat. Nos. 4,304,767 and 4,903,709, the complete disclosures of which are hereby incorporated by reference.

Our elastomers can also be modified by adding appropriate fillers, plasticizers and stabilizers (e.g., antioxidants) such as those described in the "Encyclopedia of Polymer Science and Technology", Fillers, Vol. 6, p. 740; Plasticizers, Vol. 10, p. 286; Antioxidants and Stabilizers, Vol. 2, pg 171. (John Wiley & Sons, Inc., New York).

Fillers serve as reinforcing agents and processing aids and can include: silicates such as clay, talc, feldspar, calcium silicate, and magnesium silicate; oxides such as aluminum oxide, titanium dioxide, zinc oxide, magnesium oxide, silica, quartz, and diatomaceous earth; carbonates such as calcium carbonate, barium carbonate and magnesium carbonate; sulfates such as barium sulfate and calcium sulfate; carbons such as carbon black and; polymeric fibers such as KEVLAR ® aramid pulp (KEVLAR ® is a registered trademark of the Dupont Corporation).

Plasticizers can also be added to the elastomers of the present invention, e.g., to lower the glass transition temperature, Tg. Such plasticizers include plasticizing oils such as SUNDEX ® 170 (SUNDEX ® is a registered Trademark of the Sun Oil Co.); phthalic esters; citrate esters; phosphate esters; adipic esters; azelaic esters; stearic esters; and complex linear polyesters and polymeric plasticizers.

Antioxidants retard oxidation and extend the polymer's useful life. They include diarylamines, substituted phenols, disubstituted cresols, bisphenols, derivatives of cathecol, benzoates and ketone-amine resins. Specific examples include butylated hydroxyanisole, butylated hydroxytoluene, propyl gallate and t-butyl hydroquinone.

The bioerodible thermoset elastomers of the present invention can be used as structural components of drug delivery devices and as tissue prostheses. They are also useful in the manufacture of matrices or other controlled release devices into which, or onto which, beneficial agents are included for subsequent use as implants or controlled release oral formulations.

One application of our thermoset polymers is in the manufacture of gastric retention devices such as those described in U.S. Pat. Nos. 4,735,804 and 4,758,436. In one form, the retention device is compressed within a gelatin capsule which dissolves in the stomach subsequent to ingestion. Upon dissolution of the capsule, the compressed retention device expands due to elastic forces to a size or shape that prevents it from exiting the stomach. The acidic environment of the stomach eventually degrades the device permitting exit from the stomach. Our thermoset, covalently cross-linked elastomers are uniquely suited to this application because they are bioerodible and because they retain their resiliency after compression for extended periods of time.

Our bioerodible, thermoset, covalently cross-linked elastomers may also serve as matrices for the controlled release of drugs. A drug may be associated with the matrix in different ways, depending on the physical and chemical properties of the drug. For example, the drug may be dispersed as a solution or suspension within the erodible elastomeric polymer matrix. As the matrix erodes within the gastrointestinal tract or implant site, the drug is released at a controlled rate.

The amount of drug or beneficial substance incorporated into the polymer matrix will vary greatly depending on the particular drug, the desired therapeutic effect and the time span over which the polymer matrix is eroded to release the particular drug. Thus, there is no critical upper limit to the amount of drug incorporated into the erodible elastomeric polymer matrix. In general, the amount of polymer employed in the practice of the invention will usually range from about 10% to 99% by weight of the device. The remaining portion of the composition contains the drug, and other excipients and additives.

EXAMPLES

When exposed to simulated gastric fluid (pH 1.25) the example elastomers hydrolytically degrade to regenerate the polyols, pentaerythritol dipropionate, and pentaerythritol.

Figure 2:
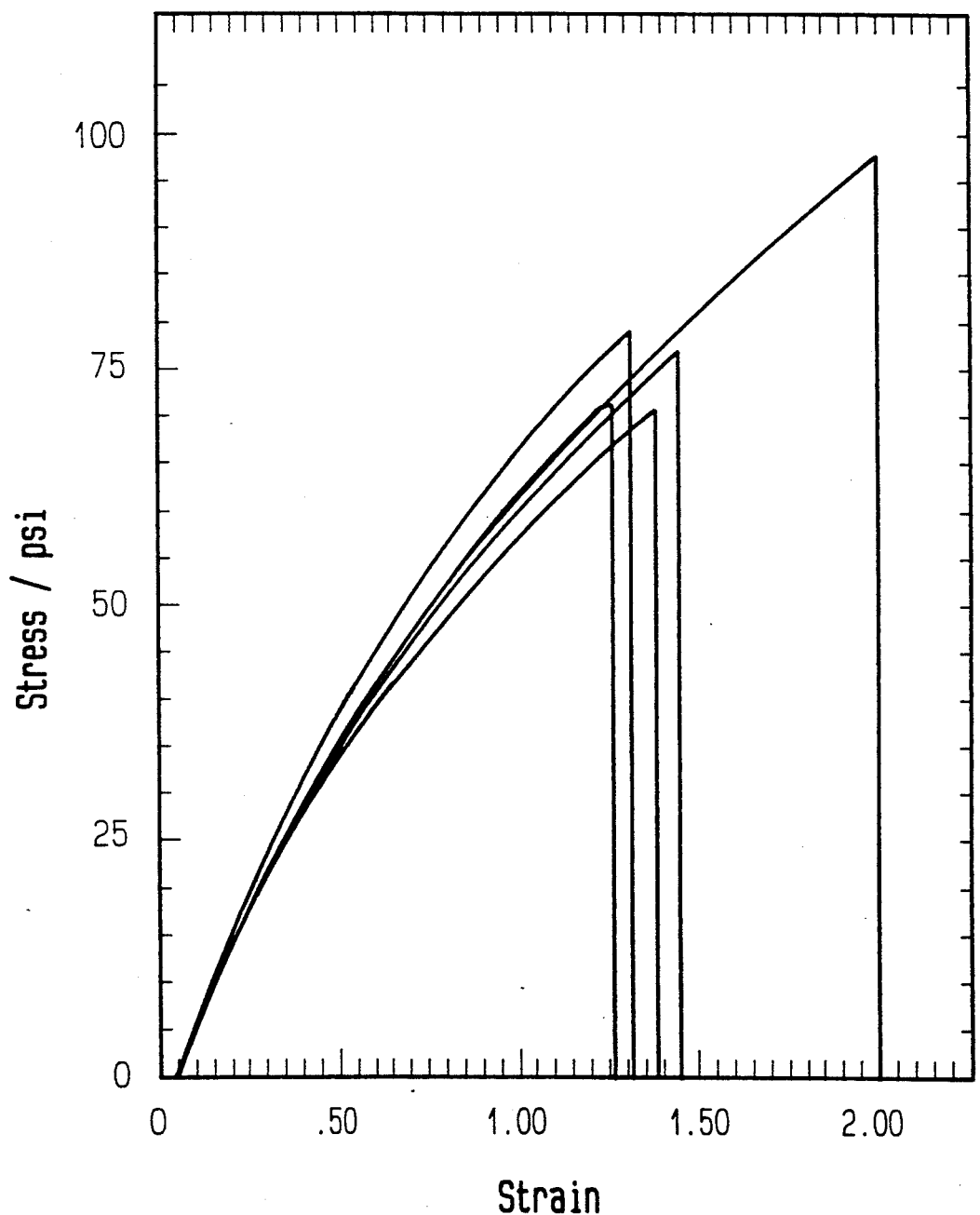
FIG. 2: is the stress/strain curve for the polymer samples of Example 1.
Figure 3:
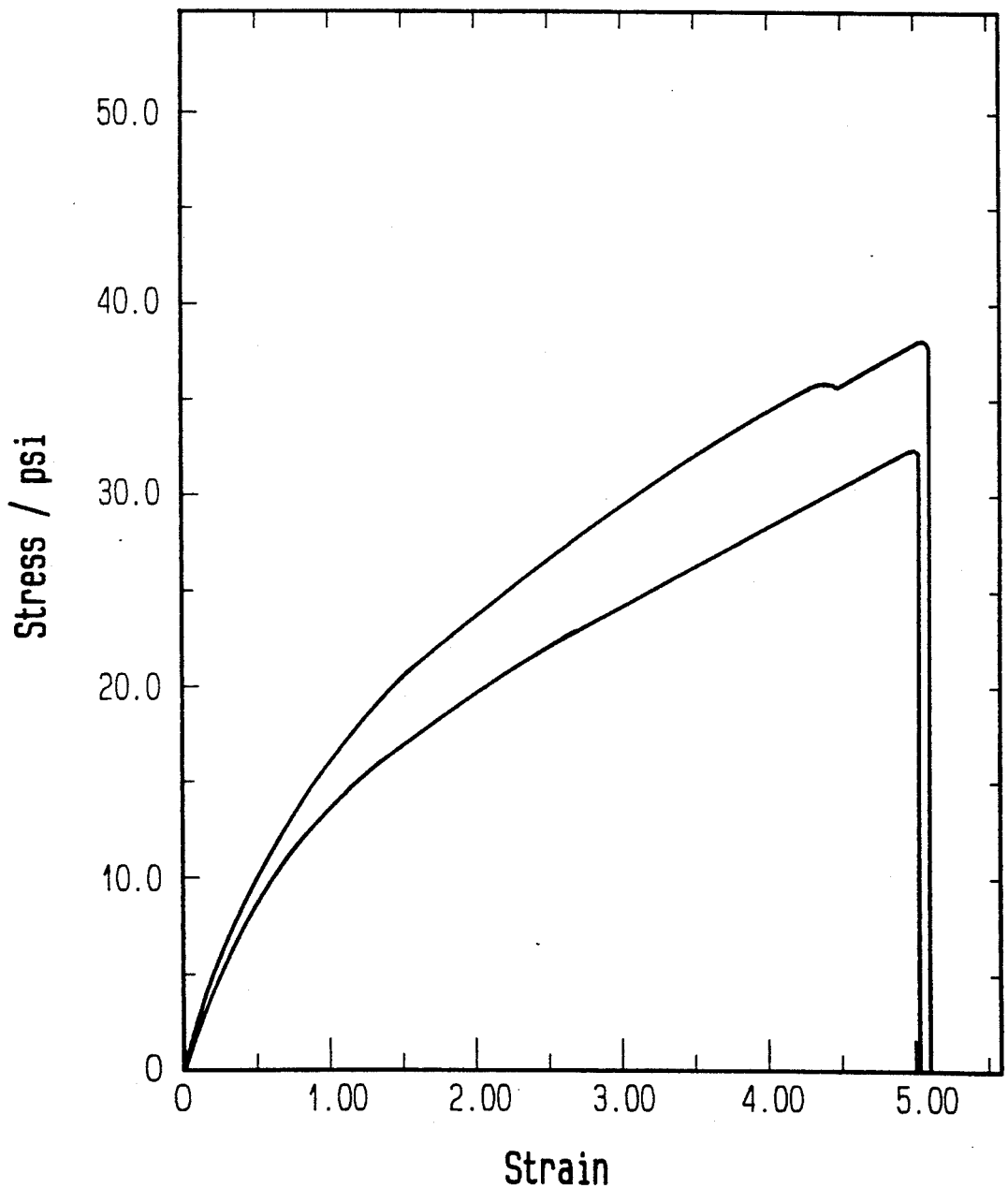
FIG. 3: is the stress/strain curve for polymer samples of Example 2.

FIGS. 2 and 3 show the elongation of elastomeric samples #1 and #2 as a function of force/unit area (Instron ™ data). The absence of yield-upon-elongation indicates good resilience. Polymers that yield with elongation will not recover the initial configuration (poor resilience) and are considered poor elastomers. While other properties (tensile or otherwise) can be used to characterize elastomeric nature, the property of reversible elongation or reversible deformation is a desirable characteristic of an elastomeric polymer. FIGS. 2 and 3 show that sample #1 is stronger (harder) than sample #2.

The invention is further illustrated by the following examples.

EXAMPLE 1

Reaction of 3,9-bis(ethylidene 2,4,8,10-tetraoxaspiro [5.5]undecane) (DETOSU) with Poly(butadiene) hydroxy terminated (PBD) and 1,2,6-hexanetriol (HT) (S=1.0, HT=5% w/w)

141.8 g PBD (approximate molecular weight 4,900; hydroxyl number 46.6 mg KOH/g polymer) was poured into a reaction kettle. To this was added HT (7.44 g) and 177 mg of butylated hydroxytoluene (BHT; antioxidant). The mixture was heated to 90° C. and vigorously stirred for 30 minutes with an overhead stirrer to effect mixing. While stirring continuously, the mixture was allowed to cool to room temperature (approximately 20° C.), then DETOSU (28.9 g) was added via syringe. Stirring was continued for 5 minutes. The resulting viscous polymer was removed from the reaction kettle, molded between steel plates lined with Teflon ™ under pressure to form sheets, and cured at 60° C. for 12 hours. The elastomer thus obtained was labelled sample #1. The tensile properties of sample #1 analyzed with an INSTRON ™ instrument. The properties of the final poly(ortho ester) are determined by the nature of the reactant polyols and diketene acetal(s) and by the stoichiometry (S) and crosslinker content (wt % crosslinker) of the reaction mixture where $$S = (\text{ketene acetal equivalents})/(\text{hydroxyl equivalents})$$

and the weight percent of crosslinker is:

$$\text{wt \% crosslinker} = \frac{(\text{crosslinker})g}{(\text{crosslinker} + \text{polymeric polyol})g} \times 100$$

The crosslink density of the synthesized polymer is directly proportional to the weight percent of crosslinker and to the functionality (the hydroxyl number) of the polymeric polyol used. The synthesis of the elastomers is depicted in the generalized overall reaction scheme of FIG. 1 where the R of the generalized diketene acetal structure represents a quadrivalent grouping that is part of a spiro or a non-spiro structure. The tensile behavior (Instron test) of our polymer samples is shown in FIG. 2 and the summarized properties are listed in Table 1.

TABLE 1

TENSILE PROPERTIES[a] OF POLY(ORTHO ESTER) ELASTOMERS

| Sample (n = 5) | S[b] | HT (% w/w) | Modulus (psi) | Tensile strength (psi) | Toughness (psi) | Break strain (%) |
|---|---|---|---|---|---|---|
| #1 | 1.0 | 5 | 91.9 ± 5.8 | 79.1 ± 10.9 | 68.2 ± 25.5 | 143.4 ± 29.7 |
| #2 | 1.0 | 0 | 30.5 ± 2.3 | 35.2 ± 4.1 | 115.5 ± 16.3 | 502.5 ± 5.0 |

[a]The data was obtained with an INSTRON ® using an ASTM D-638 type-IV die (elastomeric) with a 50 Kg load cell with flat faced serrated grips (distance between grips 3 inches); crosshead speed = 2 inch/min; gauge length = 1.3 inches.
S[b] = Stoichiometry.

EXAMPLE 2

Reaction of DETOSU with PBD (S=1.0, HT(% w/w)=0%)

The procedure of Example 1 was followed except that HT was omitted. The elastomer synthesized was labelled sample #2. The tensile properties of sample #2 were analyzed and are illustrated in FIG. 3 and summarized in Table 1.

EXAMPLE 3

Figure 4:
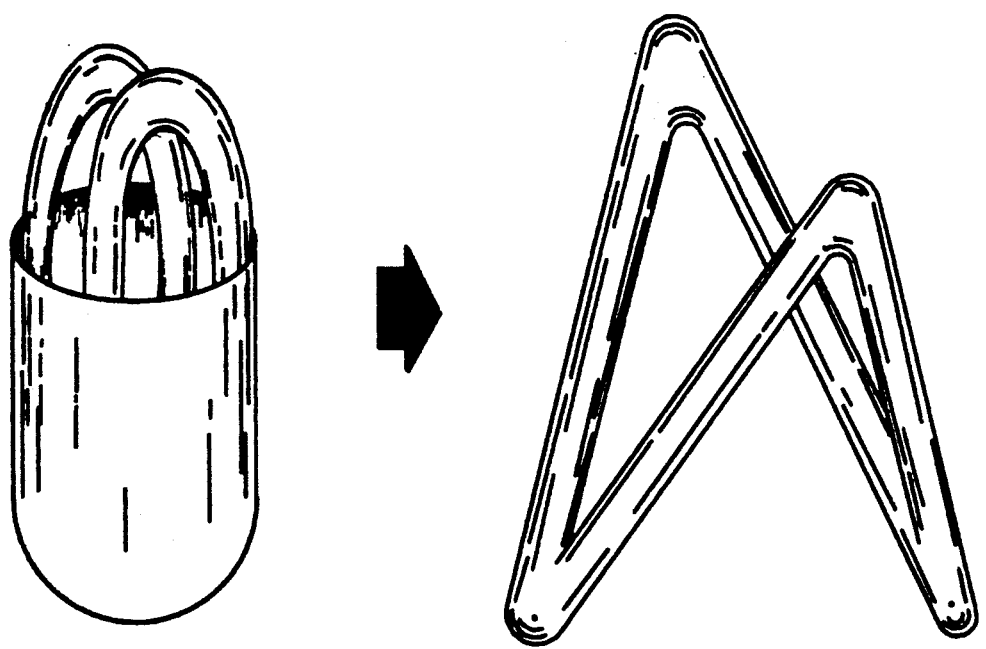
FIG. 4: illustrates a controlled release device manufactured in accordance with the instant invention.

DETOSU is reacted with PBD, PIBD, PIPD, or PDMSD, in the presence of varying amounts of cross-linker (0 to 50% w/w) in the manner described in Examples 1 and 2. The elastomers thus synthesized are used to fabricate the tetrahedral device of FIG. 4. The open tetrahedron measures 2×2×2 cm and when compressed fits into a No. 000 gelatin capsule. A biologically active compound may be incorporated into the elastomer.

EXAMPLE 4

Reaction of DETOSU with PBD (S=0.8, HT=30% w/w, MgO=0.1% w/w)

PBD (82.2 g), HT (35.4 g), BHT (190 mg), MgO (195 mg) were mixed in a Helicone ™ (Atlantic Res. Co., Gainesville, Va.) mixer at 60° C. for 1 hour under vacuum (to degas components). Magnesium oxide served to retard the polymerization rate (upon the addition of DETOSU) thereby allowing an adequate mixing time and avoiding premature curing (scorching) inside the mixer. After cooling the mixture to 40° C., the vacuum was released and DETOSU (72.66 g) was added. Mixing was continued (without vacuum) for 20 minutes. The extent of the reaction was monitored by analyzing the viscosity of the mixture every 5 minutes. The viscous polymer was transferred from the mixer into a Teflon ™-lined mold and cured into a sheet at 60° C. for 18 hours.

EXAMPLE 5

Reaction of DETOSU with PBD (S=1.2, HT=30% w/w, MgO=0.1% w/w).

The procedure of Example 4 was followed except that the stoichiometry (S) was equal to 1.2. This was accomplised by increasing the DETOSU level to 90.82 g.

EXAMPLE 6

Reaction of DETOSU with PBD (S=1.2, HT=30% w/w, MgO=0.1% w/w).

The procedure of Example 4 was followed except that the stoichiometry (S) was equal to 1.2. This was accomplished by increasing the DETOSU level to 108.98 g.

What is claimed is:

1. A controlled release device comprising a bioerodible, thermoset, covalently cross-linked, poly(ortho ester) elastomeric matrix, synthesized by the reaction of a diketene acetal with a hydroxy terminated polymeric polyol having a hydroxy functionality of at least two or with both a hydroxy terminated polymeric polyol having a hydroxy functionality of at least two and a monomeric polyol having a hydroxy functionality of at least three, the matrix containing at least one, physically admixed beneficial agent which is released in a controlled fashion from the matrix upon exposure to an aqueous environment of use.

2. The device of claim 1, as a gastric retention device comprising:
   (a) a bioerodible, thermoset, covalently cross-linked poly(ortho ester) elastomeric matrix synthesized by the reaction of a diketene acetal with (i) a polymeric polyol having a hydroxy functionality of at least two and (ii) 0 to 50% by weight of monomeric polyol, based on the total weight of (i) and (ii), having a hydroxy functionality of at least three; and
   (b) a beneficial agent (i) admixed with said elastomeric matrix or (ii) attached to said elastomeric matrx;

said elastomeric matrix expanding from a compressed state to an expanded state, and thereafter degrading in a controlled manner upon exposure to an aqueous environment of use.

3. The device of claim 2, further comprising a gelatinous coat surrounding said elastomeric matrix while in its first compressed state, said gelatinous coat substantially immediately dissolving upon exposure to an acidic environment of use.

* * * * *